United States Patent [19]

Miller

[11] Patent Number: 5,407,801

[45] Date of Patent: Apr. 18, 1995

[54] FORMATION OF OLIGONUCLEOTIDE TRIPLEXES WITH SELECTIVELY MODIFIED CYTOSINES

[75] Inventor: Paul S. Miller, Baltimore, Md.

[73] Assignee: The Johns Hopkins University, Baltimore, Md.

[21] Appl. No.: 101,094

[22] Filed: Aug. 3, 1993

Related U.S. Application Data

[63] Continuation of Ser. No. 830,574, Feb. 5, 1992, abandoned.

[51] Int. Cl.$^6$ .......................... C12Q 1/68; C07H 21/04
[52] U.S. Cl. ..................................... 435/6; 536/25.32; 536/25.3
[58] Field of Search .......................... 435/6; 536/25.32; 436/94

[56] References Cited

U.S. PATENT DOCUMENTS 5,082,935 1/1992 Cruickshank .................... 536/27

OTHER PUBLICATIONS

Viscidi, R. P. et al. Novel chemical method for the preparation of nucleic acids in nonisotopic hybridization (J. Clin. Microbiol. (Feb. 1986) 23:311–317).

Ito, T., et al. Sequence-specific DNA purification by triplex affinity capture. (Proc. Natl. Acad. Sci. USA (Jan. 1992) 89:495–498.

Maher III, L. J., et al., Inhibition of DNA Binding Proteins by Oligonucleotide-Directed Triple Helix Formation. Science (Aug. 18, 1989) 245:725–730.

*Primary Examiner*—Margaret Parr
*Assistant Examiner*—David Schreiber
*Attorney, Agent, or Firm*—Cushman Darby & Cushman

[57] ABSTRACT

An oligonucleotide or analog thereof including a single cytidine residue at a selected position and having one or more cytidine residues which are 5-methyl substituted. The cytidine nucleus can be selectively transaminated to include an aminoalkyl or carboxyalkyl group as a linker for other functional groups which can be used to form DNA duplexes and triplexes.

5 Claims, 8 Drawing Sheets

R
a = H
b = (CH$_2$)$_3$COOH
c = (CH$_2$)$_4$NH$_2$
d = (CH$_2$)CH$_3$
e = dr = deoxyribose

C≡G

T=A

FORMATION OF OLIGONUCLEOTIDE TRIPLEXES WITH SELECTIVELY MODIFIED CYTOSINES

This application is a continuation of application Ser. No. 07/830,574, filed Feb. 5, 1992, abandoned.

The present invention relates to novel oligonucleotides and functional derivatives thereof. More specifically, the invention is concerned with the selective modification of cytosines in oligonucleotides.

The research described herein was supported by a grant from the National Institutes of Health (GM45012).

BACKGROUND

Oligonucleotides and oligonucleotide analogs conjugated with functional groups have unusual properties which make them useful as hybridization probes and antisense reagents (1–3). These functional groups can include intercalators such as acridine, reporter groups such as fluorescent or spin labels, immunoreactive groups such as biotin, or chemically reactive groups such alkylating groups, psoralen or metal chelators. See, for example, U.S. application Ser. No. 06/924,234 filed Oct. 28, 1986, abandoned the disclosure of which is incorporated herein by reference.

The functional groups are usually conjugated with the oligomer via a linker arm of variable chain length. The linker arm in turn may be attached to the 3' or 5' end of the oligomer, to the internucleotide linkage of the oligomer or to a modified base located at a specific site within the oligomer.

A variety of methods are available for introducing the linker into the oligomer. Solid phase supports have been developed which incorporate a linker as part of the support (4–9). These allow synthesis of oligomers with linkers usually consisting of an aminoalkyl chain at the 3' end of the molecule. Linkers may be introduced at the 3'- or 5'-position by derivatization of terminal phosphate groups with diaminoalkanes or amino acids (10–14). H-phosphonate chemistry has been used to introduce linkers at specific internucleotide linkages within the oligomer (15–18). Protected phosphoramidite reagents and nucleoside phosphoramidite synthons have been developed which allow incorporation of linkers or linker-modified nucleosides during the course of oligonucleotide synthesis (19–23).

It is also known that aminoalkyl groups may be selectively incorporated at the $N^4$-position of cytosine by means of a bisulfite-catalyzed transamination reaction (24). This bisulfite-catalyzed transamination reaction is relied upon to provide the novel oligonucleotides of the invention.

SUMMARY OF THE INVENTION

The present invention is based on the finding that it is possible to use the bisulfite-catalyzed transamination reaction to selectively introduce aminoalkyl or carboxyalkyl linker arms at a specific deoxycytidine site within oligonucleotides or analogs thereof which also contain one or more 5-methyldeoxycytidine residues. This enables the provision of oligonucleotides and analogs thereof which contain a single amine or carboxylic acid functionality at a desired deoxycytidine site, which can serve as a linker arm for further selective attachment of a variety of functional groups. The resulting linker arm-conjugated oligomers are capable of forming stable duplexes with complementary single-stranded oligodeoxyribonucleotides as well as triple-stranded structures with target oligodeoxyribonucleotides duplexes.

One unexpected aspect of the invention is the finding that 5-methyldeoxycytidine is inert when subjected to bisulfite-catalyzed conditions for transaminating deoxycytidine. This means, for example, that when it is desired to introduce an aminoalkyl or carboxyalkyl linking group in the $N^4$-position of a particular deoxycytidine site in an oligonucleotide containing two or more deoxycytidine residues, all of such residues but the site of interest can be rendered inert to transamination by modifying such other deoxycytidine residue base or residues, to include a 5-methyl group. This then leaves only the selected deoxycytidine residue for transamination at the $N^4$-position.

The invention thus provides an oligonucleoside, e.g. oligodeoxyribonucleotide or analog thereof which includes only a single cytidine residue at a selected position with one or more other such residues being 5-methyl substituted so as to be inert to transamination reaction.

The invention also contemplates such oligonucleotides wherein the single cytidine residue is transaminated to include an aminoalkyl or carboxyalkyl group with or without one or more further functional groups attached thereto.

Another unique aspect of the invention is the finding that the oligonucleotides of the invention effectively hybridize to form stable duplexes with complementary single stranded oligonucleotides as well as triple-stranded structures with target duplexes, the 5-methyl substitution on the thus modified cytidine residues not affecting hybridization properties with otherwise complementary DNA.

DETAILED DESCRIPTION

The modified oligonucleotides of the invention or analogs thereof, e.g. oligodeoxyribonucleotides, may have any desired length and sequence but should include two or more cytidine residues, one of which is at the site where it is desired to introduce an aminoalkyl or carboxyalkyl linkage or linker arm for subsequent addition of a functional group such as psoralen, to the oligonucleotide. Other cytidine residues which are not at the desired site are converted to 5-methyl cytidine residues of the formula:

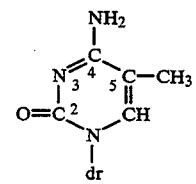

where dr represents, for example, the balance of an oligodeoxynucleotide.

The methylation of the cytidine residues may be carried out after the oligodeoxyribonucleotide is constructed or as part of the construction as the various bases are put together.

As noted earlier, it has been found, according to the invention, that 5-methyldeoxycytidine residues are not responsive to the bisulfite-catalyzed transamination reaction which is otherwise site-specific to only the remaining deoxycytidine residue. In this way, the desired aminoalkyl or carboxyalkyl linker is added to the desired site.

The present oligonucleotides may comprise any sequence of the bases A, G, C, and T with any desired number of nucleosides. Typically, the oligonucleotide may include 6–15 or more nucleosides. The A, G, T bases are inert to the transamination reaction and it is only essential that all cytidine residues in the oligonucleotide include a 5-methyl substituent except for the cytidine residue at the site selected for transamination.

BRIEF DESCRIPTION OF THE DRAWINGS

Features of the invention are illustrated by reference to the accompanying drawings herein.

Figure 1:
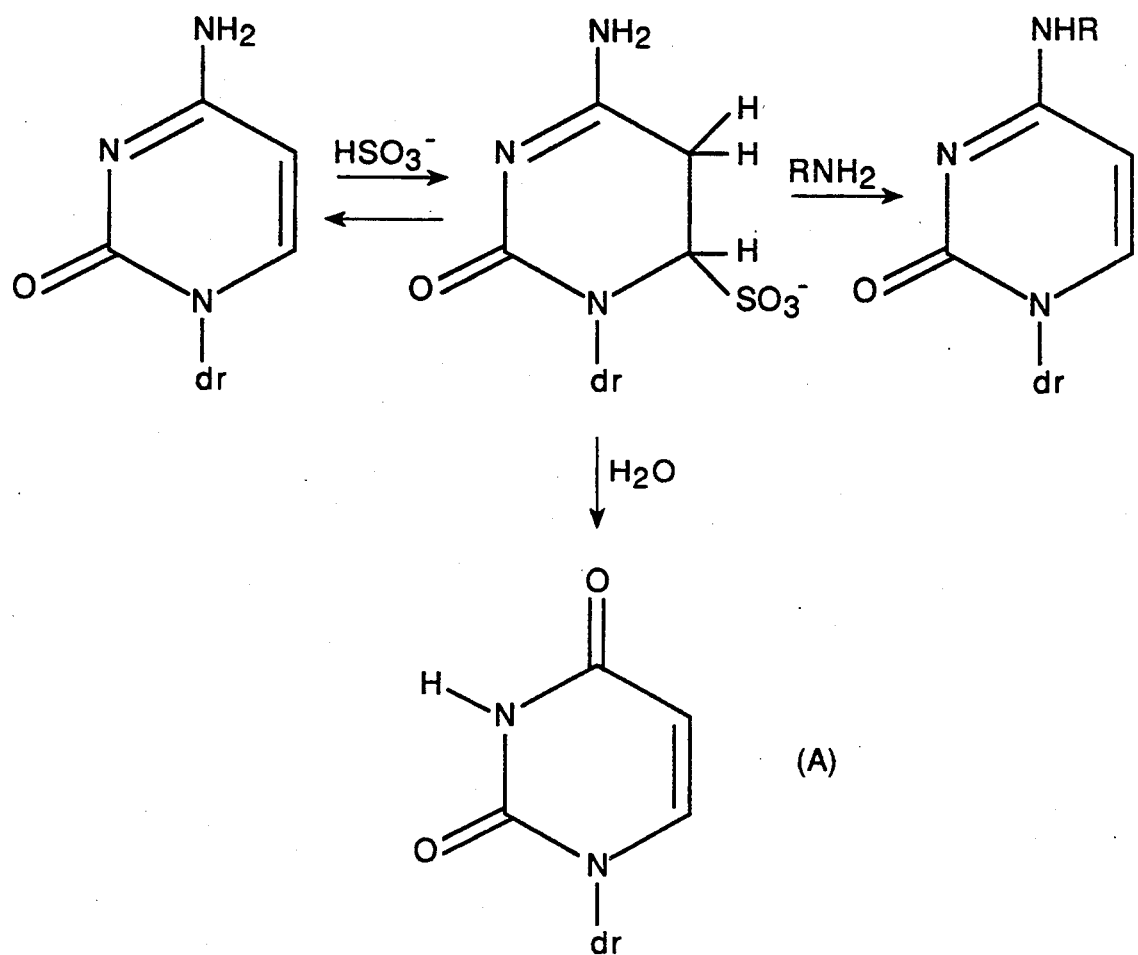
FIG. 1 illustrates the bisulfite-catalyzed transamination and deamination of deoxycytidine.
Figure 1:
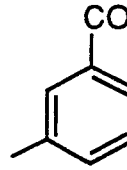

As noted, the bisulfite-catalyzed transamination and deamination of deoxycytidine are illustrated in FIG. 1 where R and dr have the meaning indicated. The transamination is represented by the product bearing the $^4$NHR substituent while the deaminated product is shown at (A).

The reaction conditions should be selected to favor transamination over deamination. Such conditions can be varied although optimum results are obtained over a relatively narrow pH and temperature range. Thus, while a pH below about 6.4 can be used, it is preferred not to go significantly below 6.0 to minimize deamination (see compound A of FIG. 1). At the other end, the pH can be as high as about 8.5–9 although the rate of transamination is reduced at the higher pHs. Preferably a pH in the range of about 7–7.5 is used.

Other conditions for the transamination e.g., temperature and time, can also be varied. Usually the temperature will be in the range of 25° to 100° C., preferably 50°–75° C. The reaction time will vary depending on the reaction temperature and pH but usually will be in the range of 12–48 hours.

The reactant $RNH_2$ is advantageously 4-aminobutyric acid (R=b in FIG. 1) although equivalent results are also obtained using, for example, 1,4-diaminobutane, aminobutane or 3-aminobenzoic acid (R=c, d or e, respectively, in FIG. 1). However, other $RNH_2$ reactants may also be used including, for example, any monoaminoalkane or diaminoalkane of up to typically 8 carbon atoms, or amino group- or dicarboxylic acids such as aminopropionic acid or the equivalent.

The invention is described in more detail in the following examples:

EXAMPLE 1

Oligonucleotide Synthesis

Oligodeoxyribonucleotides described herein were synthesized on a one μmole scale on controlled pore glass supports with commercially available base protected 5'-O-dimethoxytrityldeoxyribonucleoside-3'-O-bis(diisopropyl) amino-β-cyanoethyl phosphoramidite synthons using a Biosearch 8700 DNA synthesizer. The oligomers were deprotected and removed from the support by treatment with a solution containing pyridine/concentrated ammonium hydroxide (1:1 v/v) for 5 hrs. at 60° C. The support was removed by filtration and the solvents were evaporated. The residue was dissolved in water and the solution was loaded onto a BioGel TSK-DEAE-5-PW HPLC ion exchange column (7.5×75 mm). The column, which was monitored at 254 nm, was eluted with a 50 ml linear gradient of 0.1M to 0.5M sodium chloride in 10 mM tris hydrochloride at ph 0.0 at flow rate of 0.8 ml/min. The solution containing the oligomer was loaded onto a SEP-PAK cartridge which had been previously equilibrated with the following solutions: 10 ml of acetonitrile; 10 ml of acetonitrile/water (1:1 v/v) and 10 ml of 0.1M sodium phosphate buffered at pH 5.8. The SEP-PAK cartridge was washed with 10 ml of water and the oligomer was eluted with 3 ml of acetonitrile/water (1:1 v/v). The purity of the oligomer was checked by gel electrophoresis on a 15% denaturing gel after the oligomer had been phosphorylated using y-[$^{32}$P]-ATP and polynucleotide kinase (25). Each oligomer migrated as a single-band on the gel.

EXAMPLE 2

Transamination

Transamination solutions were freshly prepared by mixing the appropriate components as described in Table 1. The final pH of each solution was 7.1. The nucleoside (24 $A_{254}$ units, −3.5 μmoles) or oligonucleotide (10 $A_{254}$ units, −96 μmoles) was dissolved in 96 μL of transamination solution containing 4 μL of 0.1M hydroquinone in 95% ethanol. The solution was incubated for 48 hrs. at 50° C. The reaction mixture was diluted with 1 mL of 0.1M sodium phosphate buffered at pH 5.8. The oligonucleotide was purified by preparative reversed phase HPLC on a Whatman Partisil 5 RAC ODS-3 10 cm column. The column was eluted with a 50 ml linear gradient of 2% to 20% acetonitrile in 0.1M sodium phosphate, pH 5.8,- at a flow rate of 2.5 mL/min. The fraction containing the pure oligomer was diluted with 0.1M sodium phosphate to give a final acetonitrile concentration of 5% and the solution was desalted on a SEP PAK cartridge as described above.

TABLE 1

| | Transamination Solutions | | | |
|---|---|---|---|---|
| Amine (mmoles) | Sodium Bisulfite mg | Water ml | 8N Sodium Hydroxide ml | 12N Hydrochloric Acid ml |
| 4-aminobutyric acid (3.0) | 104 | 0.90 | 0.10 | — |
| 1,4-diaminobutane (3.0) | 104 | 0.30 | — | 0.47 |
| 1-aminobutane | 104 | 0.80 | — | 0.20 |

TABLE 1-continued

| | Transamination Solutions | | | |
|---|---|---|---|---|
| Amine (mmoles) | Sodium Bisulfite mg | Water ml | 8N Sodium Hydroxide ml | 12N Hydrochloric Acid ml |
| (3.0) | | | | |

EXAMPLE 3

Transamination of Deoxycytidine with 4-Aminobutyric Acid

A solution of deoxycytidine, 48 $A_{254}$ units (7.7 μmoles) in 12 μL of water was added to 180 μL of transamination buffer prepared as described in Table 1 and 8 μL of 0.1M hydroquinone in 95% ethanol. The solution was incubated at 50° C. for 48 hrs. and then treated with 1 mL of 0.1M sodium hydroxide at room temperature for 2 hrs. The solution was passed through a Dowex 50X column which contained 1 mL of resin in the pyridinium form. The column was washed with 3 ml of water and the combined eluant and washings were evaporated to dryness. The residue was dissolved in 0.6 mL of water and the product purified by reversed phase HPLC on a Partisil 5 RAC ODS-3 10 cm column. The column was eluted with 30 mL of a linear gradient of 0% to 3% acetonitrile in 0.1M sodium phosphate at a flow rate of 2.5 mL/min. A total of 28 $A_{254}$ units were obtained. The UV spectrum showed $y_{max}$ at 239 nm, 271 nm and $y_{min}$ 230 nm, 250 nm in 0.1M sodium phosphate, pH 5.8. The proton nmr spectrum in $H_2O$ showed the following resonances: multiplet, 1.83 ppm (—NH—CH2—CH2—COOH); multiplet, 2.23 ppm (H-2'); triplet, 2.96 ppm (—NH—CH2—CH2—CH2—COOH); triplet, 3.30 ppm (—NH—CH2—CH2—CH2—COOH); multiplet, 3.74 (H-5'); multiplet, 4.00 ppm (H-4'); multiplet, 4.39 ppm (H-3'); doublet, 5.94 ppm (H-5'); triplet, 6.24 ppm (H-1') and doublet, 7.63 ppm (H-6).

EXAMPLE 4

Transamination of Deoxycytidine and 5-Methyldeoxycytidine

In order to optimize the conditions for the transamination reaction, which is shown schematically in FIG. 1, the reaction of deoxycytidine with 4-aminobutyric acid was performed at various pHs. Reactions were carried out at pH 6.4, 7.1 or 8.2 in the presence of 1M sodium bisulfite and 3M 4-aminobutyric acid at 50° C. Hydroquinone was added to inhibit radical generated modification of the nucleoside (26). The products of the reaction were analyzed by reversed phase HPLC for $N^4$-(3-carboxypropyl) deoxycytidine and deoxyuridine. The results are shown graphically in FIG. 2 where the amount of $N^4$-(3-carboxypropyl) product and deoxyuridine obtained in plotted against time for reaction at pH 6.4 (○), pH 7.1 (□) and pH 8.2 (△), the filled symbols referring to the $N^4$-(3-carboxypropyl) product while the unfilled symbols refer to deoxyuridine.

Figure 2:
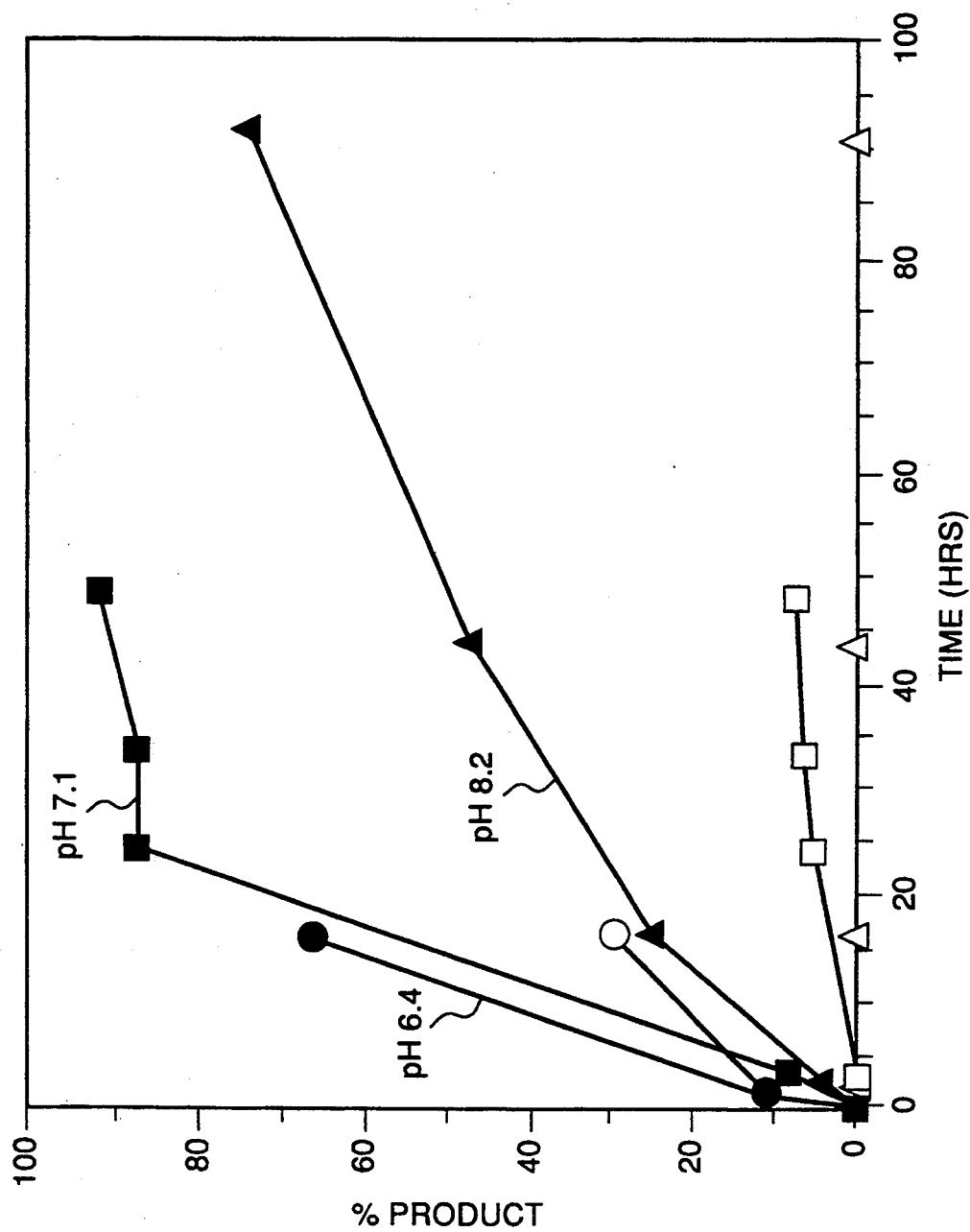
FIG. 2 graphically illustrates the rate of formation of $N^4$-(3-carboxypropyl) deoxycytidine (filled symbols) and deoxyuridine (open symbols) upon incubation of 2'-deoxycytidine with 1M sodium bisulfite and 3M 4-aminobutyric acid at 50° C. at pH 6.4 (◯), pH 7.1 (☐) or pH 8.2 (Δ)

As shown in FIG. 2, reactions carried out at pH 7.1 gave the highest yield of product and minimum amounts of deoxyuridine, a side product generated by deamination of deoxycytidine. The rate of deamination increased at pH 6.4, whereas at pH 8.2, no deamination was observed. However, at the higher pH, the rate of transamination was reduced to approximately one-fifth that at pH 7.1. The rate of transamination was also reduced when the concentrations of either sodium bisulfite or 4-aminobutyric acid were reduced or when the temperature of the reaction was reduced.

Similar results were obtained when transamination was carried out in the presence of 1,4-diaminobutane, aminobutane or 3-aminobenzoic acid. The limited solubility of the latter allowed only a 1M solution to be prepared. In this case, the extent of transamination was approximately 30% after 48 hours.

In contrast to the behavior of deoxycytidine, 5-methyldeoxycytidine was found to be completely unreactive when incubated at 50° C. in transamination buffer containing 4-aminobutyric acid at either pH 6.4, 7.1 or 8.2. The reaction of 5-methyldeoxycytidine with 1M sodium bisulfite was examined by proton nmr.

Figure 3A:
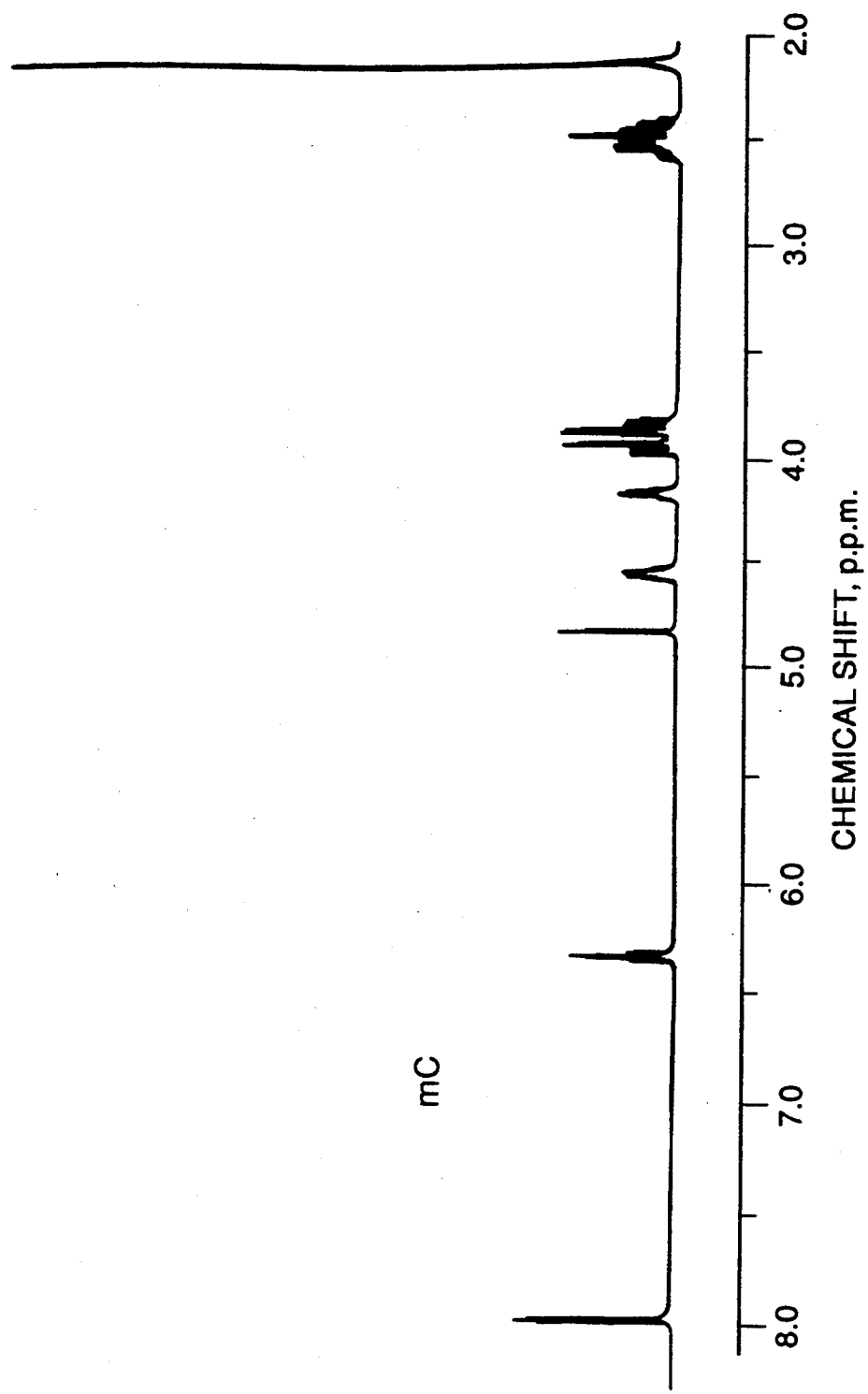
FIG. 3 is the proton nmr spectrum of (A) 5-methyl-2'-deoxycytidine or (B) 2'-deoxycytidine in 1M sodium bisulfite.
Figure 3B:
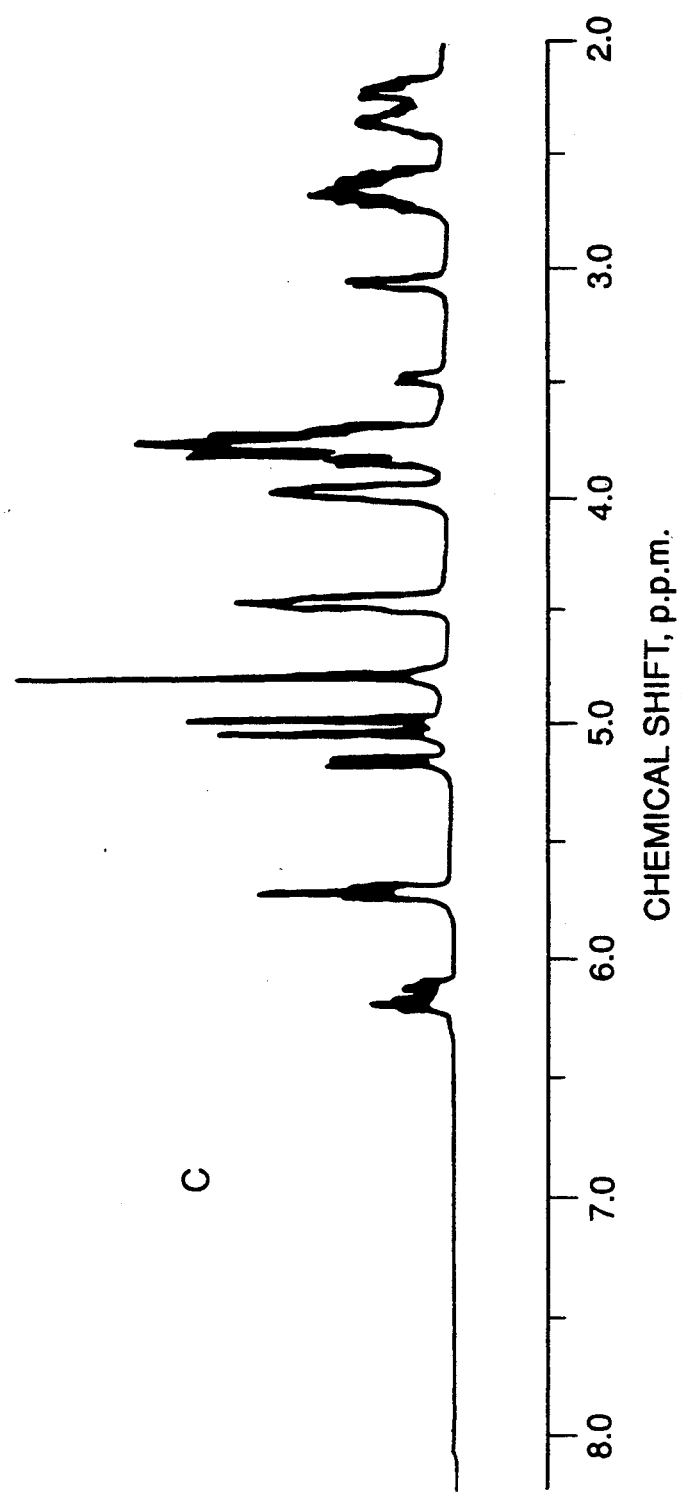

FIG. 3 represents the proton nmr spectra of (A) 5-methyl-2'-deoxycytidine or (B) 2'-deoxycytidine after contact with 1M sodium bisulfite. As there shown, incubation of deoxycytidine with 1M sodium bisulfite resulted in the disappearance of the H-5 and H-6 resonances at 6.0 and 7.7 ppm, respectively, and the appearance of new resonances at 5.0, 5.2 and 5.8 ppm which correspond to the formation of the bisulfite adduct. The appearance of two sets of sugar proton resonances, for example, the two sets of H-1' resonances at 6.1 and 6.2 ppm, suggest that the bisulfite adducts of both deoxycytidine and its deamination product, deoxyuridine are present in the reaction mixture. No change in the proton nmr spectrum of 5-methyldeoxycytidine was observed under these conditions.

The proton nmr spectra of deoxycytidine and 5-methyldeoxycytidine were obtained as follows:

Deoxycytidine, 2 mg, or 5-methyldeoxycytidine, 2 mg, were dissolved in 0.5 ml of $^2H_2O$ containing 52 mg of sodium bisulfite. The solutions were incubated overnight at room temperature and the proton nmr spectra were then recorded on a Brucker 300 MHz spectrometer using as an internal standard.

EXAMPLE 5

Transamination of Oligodeoxyribonucleotides

Two oligodeoxyribonucleotides, d-CTT·CTT·TTT·TC (Ia) Seq ID NO:1 and d-CTT·CTT·TTT·TCT·TTT (IIa) Seq ID NO:2, where C represents 5-methyldeoxycytidine and C is deoxycytidine, were synthesized. Transamination of Ia or IIa was carried out under the same conditions used to transaminate deoxycytidine. Under these conditions, little or no degradation of the oligomer was observed.

Figure 4:
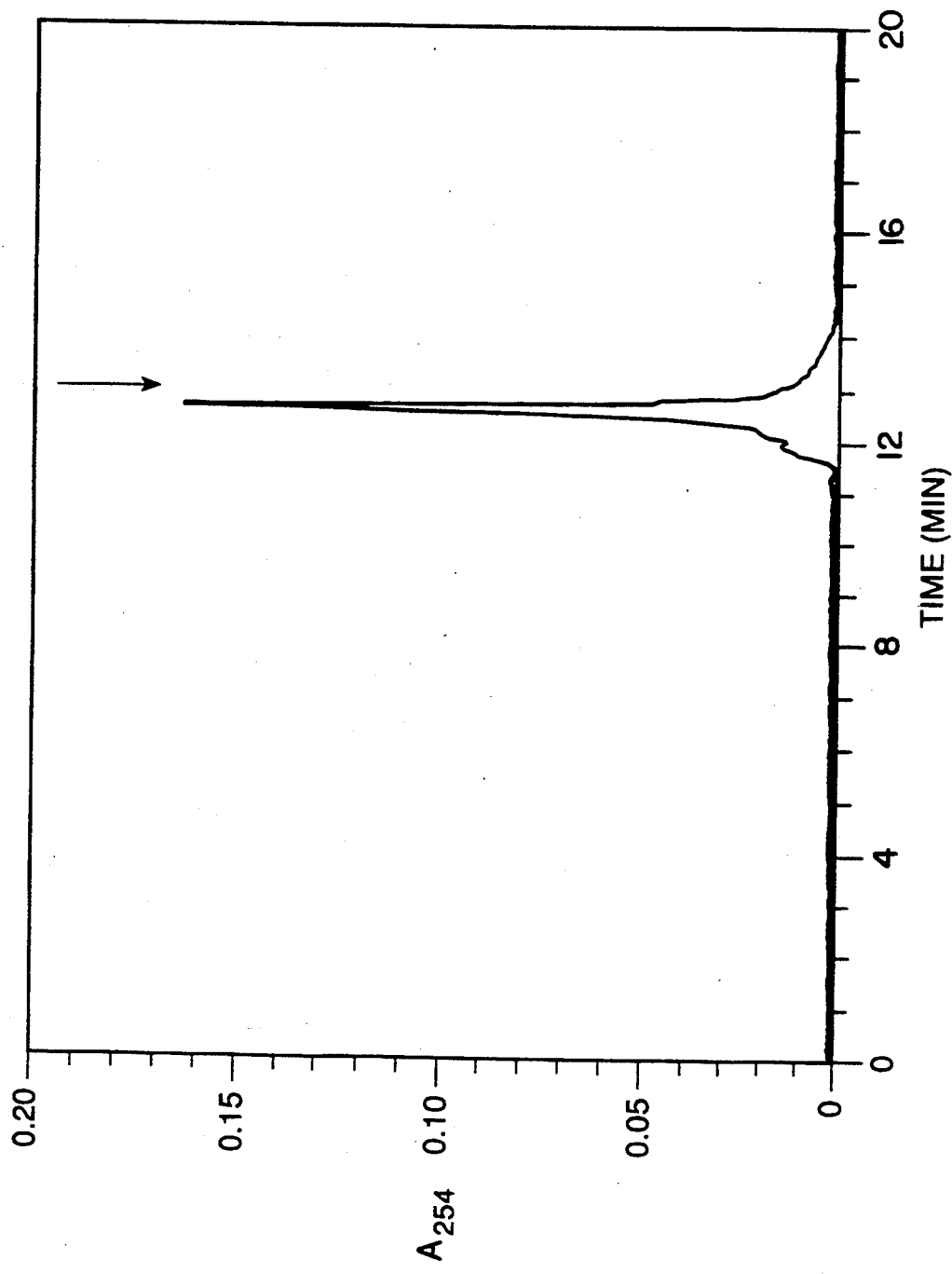
FIG. 4 is a reversed phase HPLC of the products of reaction of d-CTT-CTT-TTT-TCT-TTT with 1M sodium bisulfite and 3M 4-aminobutyric acid. The elution conditions are described hereinafter and the arrow indicates the retention time of the starting oligomer.

FIG. 4 represents a reversed phase HPLC of the products obtained by reacting oligodeoxyribonucleotide (IIa) with 1M sodium bisulfite and 3M 4-aminobutyric acid. As there shown, transamination of IIa with 4-aminobutyric acid resulted in the formation of a single major product, IIb, whose retention time on the reversed phase column was distinct from that of IIa. Transamination of Ia or IIa with 1,4-diaminobutane or 1-aminobutane also gave single products, Ic, IIc and IId, respectively, as assayed by reversed phase HPLC.

Digestion of IIb with a combination of snake venom phosphodiesterase and bacterial alkaline phosphatase yielded three nucleosides, thymidine, deoxycytidine and $N^4$-(3-carboxypropyl)deoxycytidine in the expected molar ratios as shown in Table 2. The reverse phase HPLC mobility of the latter nucleoside was identical to that of authentic $N^4$-(3-carboxypropyl)deoxycytidine produced by transamination of deoxycytidine by 4-aminobutyric acid. No deoxyuridine was detected in the digest of the oligomer. In a similar manner, oligomer IId gave the expected products thymidine, deoxycytidine and N⁴-butyldeoxycytidine following enzymatic digestion. However, digestion of oligomers Ic or IIc gave thymidine, deoxycytidine and a product whose reversed phase HPLC mobility was consistent with that of a dinucleoside monophosphate. Analysis of the base ratios suggested that the dimer was d-TpX, where X is N⁴-(4-aminobutyl)deoxycytidine. This was confirmed by preparing d-TpX by transamination of d-TpC with 1,4-diaminobutane. The reversed phase HPLC mobility of this modified dimer was identical to that of the dimer observed in the digests of the oligomers.

TABLE 2

Enzymatic Digestion of Modified Oligodeoxyribonucleotides

| Oligomer | Base Ratio | | | 260 nm |
|---|---|---|---|---|
| | d-C | d-X | d-T | |
| d-CTT.CTT.TTT.TX Seq ID NO: 3 | | | | |
| I X | | | | |
| a C | 1.0 | 0.5 | 4.1 | 84,800 |
| c N⁴-(4-aminobutyl)C | 1.0 | 0.5$^{(a)}$ | 3.6 | 68,900 |
| d-CTT.CTT.TTT.TXT.TTT Seq ID NO: 4 | | | | |
| II X | | | | |
| a C | 1.0 | 0.5 | 6.1 | 104,400 |
| b N⁴-(3-carboxypropyl)C | 1.0 | 0.6 | 6.1 | 102,200 |
| c N⁴-(4-aminobutyl)C | 1.0 | 0.6$^{(a)}$ | 5.5 | 93,600 |
| d N⁴-butylC | 1.0 | 0.6 | 5.8 | 90,800 |

$^{(a)}$d-TpX, X = N⁴-(4-aminobutyl)C

As noted, the transaminated oligodeoxyribonucleotides of the invention can be used to hybridize with complementary DNA targets. This is shown by the following:

EXAMPLE 6

Interaction of Transaminated Oligodeoxyribonucleotides with Complementary DNA Targets The ability of oligodeoxyribonucleotides Ia or IIa and their transaminated derivatives to form duplexes with the complementary single-stranded DNA target, d-AAA·AGA·AAA·AAG·AAG (III) Seq ID NO:5, was studied. The experiments were carried out in a buffer consisting of 0.1M sodium chloride, 20 mM magnesium chloride and 50 mM Tris at pH 7.0. One-to-one mixtures of the oligomers and the target gave melting curves with a single transitions. The melting temperatures of duplexes formed by the transaminated oligomers were between 2° to 4° C. lower than the comparable duplex formed by the parent oligomer a shown in Table 3.

TABLE 3

Melting Temperatures of Duplexes Containing Modified Oligodeoxyribonucleotides

| Duplex | Tm (°C.)$^{(a)}$ |
|---|---|
| d-CTT.CTT.TTT.TX | |
| GAA.GAA.AAA.AGA.AAA-d Seq ID NO: 6 | |
| Ia X = C | 40 |
| Ib X = N⁴-(4-aminobutyl)C | 37 |
| d-CTT.CTT.TTT.TXT.TTT Seq ID NO: 7 | |
| GAA.GAA.AAA.AGA.AAA-d | |
| IIa X = C | 47 |
| IIb X = N⁴-(3-carboxypropyl)C | 43 |
| IIc X = N⁴-(4-aminobutyl)C | 45 |
| IId X = N⁴butylC | 44 |

$^{(a)}$The melting temperatures were carried out at an oligomer strand concentration of 0.5 μM in 0.1M sodium chloride, 20 mM magnesium chloride, 50 mM Tris, pH 7.0 as stated.

Figure 5:
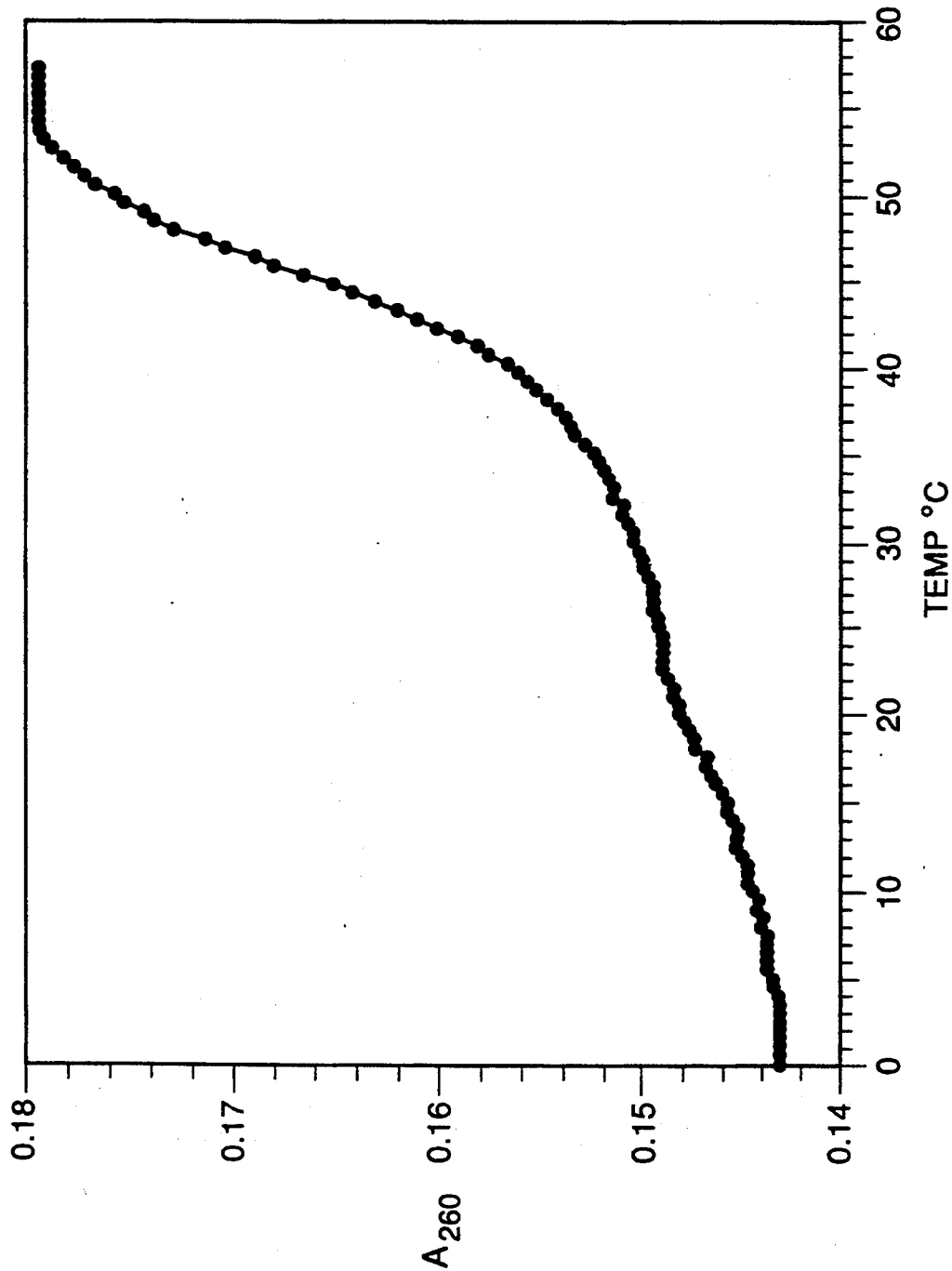
FIG. 5 is an absorbance versus temperature profile of a solution containing 0.5 μM IIb and 0.5 μM double-stranded DNA target IV in 0.1M sodium chloride, 20 nM magnesium chloride, 50 mM Tris, pH 7.0.

Transaminated 15-mers were also found to be capable of forming triple-stranded complexes with the double-stranded DNA target, d-GAA·GAA–AAA·AGA·AAA/d-TTT·TCT·TTT·TTC·TTC (IV). FIG. 5 shows that a one-to-one mixture of IIb and IV gives two cooperative transitions in a plot of $A_{260}$ versus temperature with midpoints at 16° to 45° C. The first transition corresponds to melting the third strand oligomer IIb and the second transition corresponds to melting of the target duplex IV. Similar results were obtained for the other derivatized oligomers as shown by the data in Table 4. The third strand melting temperature of the triplexes formed by the derivatized oligomers was 18° C. lower than that of the triplex formed by oligomer IIa.

TABLE 4

Melting Temperatures of Triplexes Containing Modified Oligodeoxyribonucleotides

| Triplex | Tm (°C.)$^{(a)}$ | |
|---|---|---|
| | (b) | (c) |
| d-CTT.CTT.TTT.TXT.TTT | | |
| d-GAA.GAA.AAA.AGA.AAA IV | | |
| CTT.CTT.TTT.TCT.TTT-d | | |
| IIa X = C | 34 | 45 |
| IIb X = N⁴-(3-carboxypropyl) C | 16 | 44 |
| IIc X = N⁴-(4-aminobutyl) C | 16 | 45 |
| IId X = N⁴-butyl C | 16 | 44 |

$^{(a)}$The melting temperatures were carried out at an oligomer strand concentration of 0.5 5M in 0.1M sodium chloride, 20 mM magnesium chloride, 50 mM Tris, pH 7.0.
(b) Transition from triplex to third strand + duplex.
(c) Transition from duplex to single strands.

The melting temperatures of duplexes and triplexes referred to above were determined using a Varian 219 spectrophotometer fitted with a thermostated cell compartment. The cell holder was connected to a Neslab RTE 100 circulating, programmable temperature bath. The temperature of the cell holder was monitored by a Varian temperature readout unit and the sample compartment was continuously purged with dry nitrogen throughout the experiment. All experiments were carried out in melt buffer which consisted of 0.1M sodium chloride, 20 mM magnesium chloride and 50 mM Tris hydrochloride buffered at pH 7.0. Duplexes were formed by mixing 0.5 ml of 1.0 μM solution of each oligomer. Triplexes were formed by mixing 0.5 ml of a 1.0 μM solution of the oligomer with 0.5 ml of a 1.0 μM solution of the preformed target duplex. The $A_{260}$ of the duplexes or triplexes were recorded as a function of temperature as the solutions were heated from 0° to 60° C. at a rate of 1° C./min.

In connection with the foregoing, it is noted that the following procedure was used to determine oligomer extinction coefficients:

Four samples of the oligomer (0.2 to 0.5 $A_{254}$ unit) were dissolved in 48 μL of digestion buffer. Duplicate samples of the oligomer were treated with 2 μL, 5 ng, of snake venom phosphodiesterase or with 2 μL of water. The solutions were incubated for 16 hours at 37° C. and then diluted with 1.0 ml of water. The $A_{254}$ of the enzyme-treated solutions were used to determine the amount of oligomer hydrolyzed and this amount was then used to calculate the oligomer extinction coefficient based upon the $A_{260}$ of the water-treated solutions.

Base ratios were determined as follows:

The oligonucleotide (0.2 $A_{254}$ units) was dissolved in 48 μL of digestion buffer containing 2 mM magnesium chloride and 10 mM Tris hydrochloride, pH 8.2. Snake venom phosphodiesterase, 5 ng in 2 μL, and bacterial alkaline phosphatase, 0.4 units in 2 μL, were added and the reaction mixture was incubated for 16 hours at 37° C. The solution was diluted with 200 μL of 0.1M sodium phosphate, pH 5.8. Aliquots were analyzed by reversed phase HPLC on a Whatmann ODS-3 RACII column using an 18 ml linear gradient of 0% to 3% acetonitrile in 0.1M sodium phosphate followed by a 12 ml linear gradient of 3% to 20% acetonitrile in 0.1M sodium phosphate, pH 5.8, at a flow rate of 1.5 ml/min. The column was monitored at 254 nm. Peaks corresponding to the nucleosides were cut out, weighed and normalized by dividing the weight of the peak by the extinction coefficient of the nucleoside. Alternatively, the area under the peak was determined by integration and normalized by dividing the peak area by the extinction coefficient of the nucleoside. The following extinction coefficients at 254 nm were used: 5-methyldeoxycytidine, 3,700; deoxycytidine or $N^4$-modified deoxycytidine, 6260; and thymidine, 7,250.

As earlier noted, bisulfite-catalyzed transamination is a well known reaction which has been used to modify and probe the structure of nucleic acids (24, 26–30). In this context, the reaction shows selectively for C residues which occur in single-stranded regions of nucleic acids. The reaction, however, would ordinarily not be expected to be sequence selective for C residues which occur in single-stranded oligonucleotides. The present results demonstrate that site selective transamination in oligonucleotides can be achieved by substituting 5-methylcytosine for cytosine at positions where transamination is not desired. The single remaining cytosine residue then becomes a target for transamination. Oligomers which are modified in this manner are still capable of hybridizing complementary nucleic acids because 5-methylcytosine can readily participate in normal Watson-Crick or Hoogsteen base pairing interactions which lead to the formation of double- and triple-stranded complexes, respectively.

Reaction of cytosine with bisulfite can lead to both deamination as well as transamination as is shown in FIG. 1 (24). The results shown herein are essentially in agreement with those of Draper (26), who showed that the rates of deamination and transamination are sensitive to the pH of the reaction solution. The rate of deamination appears to be accelerated at lower pH whereas deamination is suppressed at pH 7 and higher. Both deamination and transamination proceed via the bisulfite adduct which can be detected by proton nmr as shown in FIG. 3. In contrast to cytosine, 5-methylcytosine shows no evidence of forming the bisulfite adduct. Consequently, no reaction is observed when 5-methylcytidine is subjected to conditions under which deoxycytidine undergoes either deamination or transamination.

Efficient transamination of deoxycytidine is shown to have occurred when the reaction was carried out in the presence of 1M sodium bisulfite and 3M amine at pH 7.2 at a temperature of 48° C. While these conditions can be varied, it is noted that under the conditions used, the nucleoside was converted to 90% or greater of the transaminated product as determined by HPLC analysis. For example, transamination by 4-aminobutyric acid gave 93% of $N^4$-(3-carboxypropyl)deoxycytidine, 6% deoxyuridine and 1% deoxycytidine. Similar results were obtained when transamination was carried out with 1,4-diaminobutane or 1-aminobutane. Less efficient transamination was observed with 3-aminobenzoic acid, which gave $N^4$-(3-carboxyphenyl)deoxycytidine in approximately 30%. In this case, the lower extent of reaction appears to be due to the bulky nature of the amine and the lower solubility of the amine which only allowed a 1M solution to be prepared.

Conditions which lead to efficient transamination of the nucleoside also result in efficient transamination of deoxycytosine residues in oligodeoxyribonucleotides. Little or no hydrolysis of the oligomer was observed and the reaction appeared to be selective for deoxycytidine residues. Thus, treatment of d-GAA·GAA·AAA·AGA·AAA, an oligomer which contains only purine nucleosides, with 3M 1,4-diaminobutane in the presence of 1M sodium bisulfite at pH 7.2 for two days at 48° C. resulted in no change in the oligomer as judged by HPLC. This result, coupled with the observation that 5-methylcytosine is inert to transamination, indicates that transamination can be used to selectively modify C residues in an oligonucleotide which contains A,G,T and 5-Me-C.

It is also noted that oligomers Ia, IIa, IIb and IId were completely hydrolyzed to their component nucleosides when treated with a mixture of snake venom phosphodiesterase and bacterial alkaline phosphatase. The resulting nucleosides were obtained in the expected molar ratios. Essentially no deoxycytidine or deoxyuridine was observed in the digests of the transaminated oligomers IIb or IIc. This result indicates that transaminated oligomers were successfully purified from non-transaminated oligomer and that the extent of deamination, if any, was below the limits of detection by HPLC.

In contrast to the behavior of the oligomers derivatized with $N^4$-(3-carboxypropyl)cytosine or $N^4$-butylcytosine, oligomers Ib and IIb which contain a $N^4$-(4-aminobutyl)cytosine were hydrolyzed to a mixture of thymidine, 5-methyldeoxycytidine and the dimer d-Tp-[$N^4$-(4-aminobutyl)]C. It appears that the presence of the aminobutyl side chain in some manner protects the internucleotide linkage on the 5'-side of the modified base from hydrolysis by the exonucleolytic activity of the snake venom phosphodiesterase. The inhibitory effect could be due to the size of the aminobutyl side chain, although the 3-carboxypropyl side chain, which is also five atoms long, would then be expected to have similar effects. Alternatively, the primary amino group of the side chain, which should be protonated under these conditions, may directly interact with the enzyme. Based on examination of molecular models, it appears unlikely that protection arises for interaction of the protonated amino group of the aminobutyl side chain interacts with the negatively charged phosphodiester internucleotide bond.

As shown, oligomers which carry a single linker arm at the $N^4$-position of cytosine are able to form stable duplexes with complementary single-stranded DNA targets. The melting temperatures of these duplexes are only slightly less than that of the duplex formed by the unmodified oligomer. The position of the modification does not appear to effect the stability of the duplex. Thus, the duplex formed by oligomer Ib, which contains an aminobutyl group at the 3'-end of the oligomer, shows the same reduction in melting temperature as the duplex formed by oligomer IIc, which contains an internal aminobutyl group. These results suggest that the $N^4$-modified cytosines of the transaminated oligomers are able to form normal Watson-Crick base pairs with the complementary G in the target strand.

It is also shown above that the transaminated oligomers are capable of forming triplexes with a double-stranded DNA target. In this case, the melting temperature of the derivatized oligomer from the triplex is considerably lower than that of the unmodified oligomer. This decrease in stability may be due to steric interactions between the side chain and components in the major groove of the triplex although examination of molecular models suggest that the side chains should be accommodated in this environment. Alternatively, the pK of the modified cytosines may be lower than that of cytosine as a result of modification of the $N^4$-position. In this case, protonation of the modified base would be less likely to occur at pH 7.0 and the modified base would then be capable of forming only a single hydrogen bond with the 0–6 carbonyl of guanine in the G-C base pair of the target.

Oligomers carrying the 3-carboxypropyl, 4-aminobutyl or benzoic acid side chain contain reactive functional groups which allow conjugation with a variety of molecules. For example, the carboxyl group can serve as a site for carbodiimide mediated esterification or amidation, whereas the amino group should be reactive toward isothiocyanates or N-hydroxysuccinimide esters of carboxylic acids. Thus, it is contemplated that the oligomers can be conjugated with, for example, fluorescent groups such as fluorescein or tetramethylrhodamine. Based on the melting studies described above, these derivatized molecules should form stable duplexes with complementary single-stranded nucleic acids and under the appropriate conditions, triplexes with double-stranded nucleic acids.

Figure 6A:
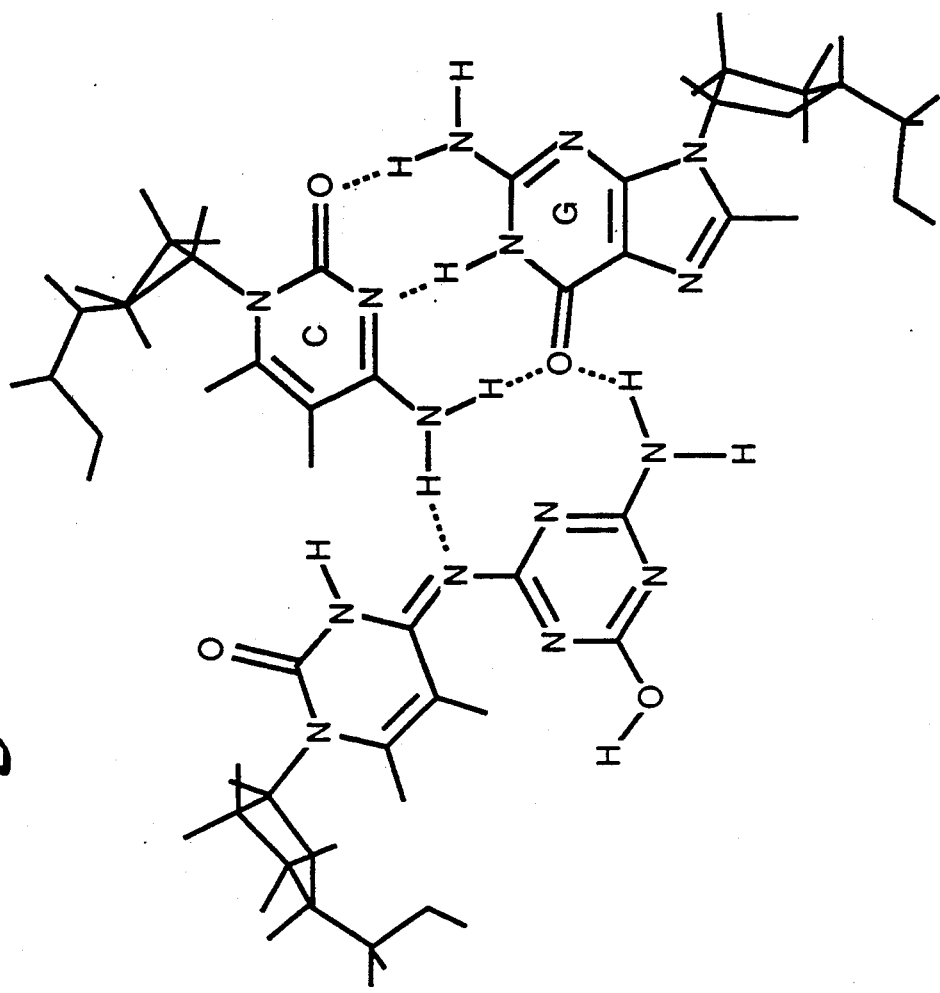
FIGS. 6 and 7 illustrate triple-stranded structures using the invention.
Figure 6B:
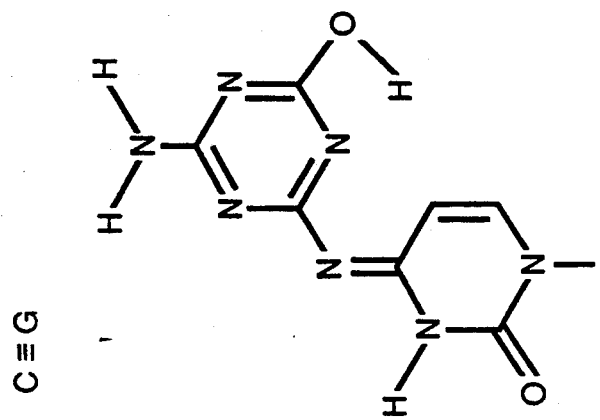

For example, the selected linker arms may include specifically designed groups which are capable of interacting with base pairs in duplex DNA or RNA to form triple-stranded structures. FIG. 6 illustrates a third structure (identified as DNA 161) in which a deoxycytidine (C) residue of an oligonucleotide or oligonucleotide analog (left side of the figure) has been modified with a 4,6-diamino-2-hydroxy-1,3,5-triazine arm using the procedure disclosed herein. This modified C residue may form hydrogen bonds with a C-G base pair of double-stranded DNA as shown in FIG. 6. This type of interaction allows suitably modified oligonucleotide or oligonucleotide analog carrying the modified C residue to interact with double-stranded DNA via triplex formation.

It will be appreciated that other substituted triazines, pyrimidines, pyridines or benzenes can also be used as linker arms in the manner described above. These include, as examples, 2,4-diamino-1,3,5-trazine, 2,4,5-triamino-1,3,5-triazine (melamine), 2,4,6-triaminopyrimidine, 2,4-diamino-6-mercaptopyrimidine, 2,4-diamino-6-hydroxypyrimidine, 2,6-diaminopyridine, m-phenylenediamine, and 3,5-diaminobenzoic acid.

Figure 7A:
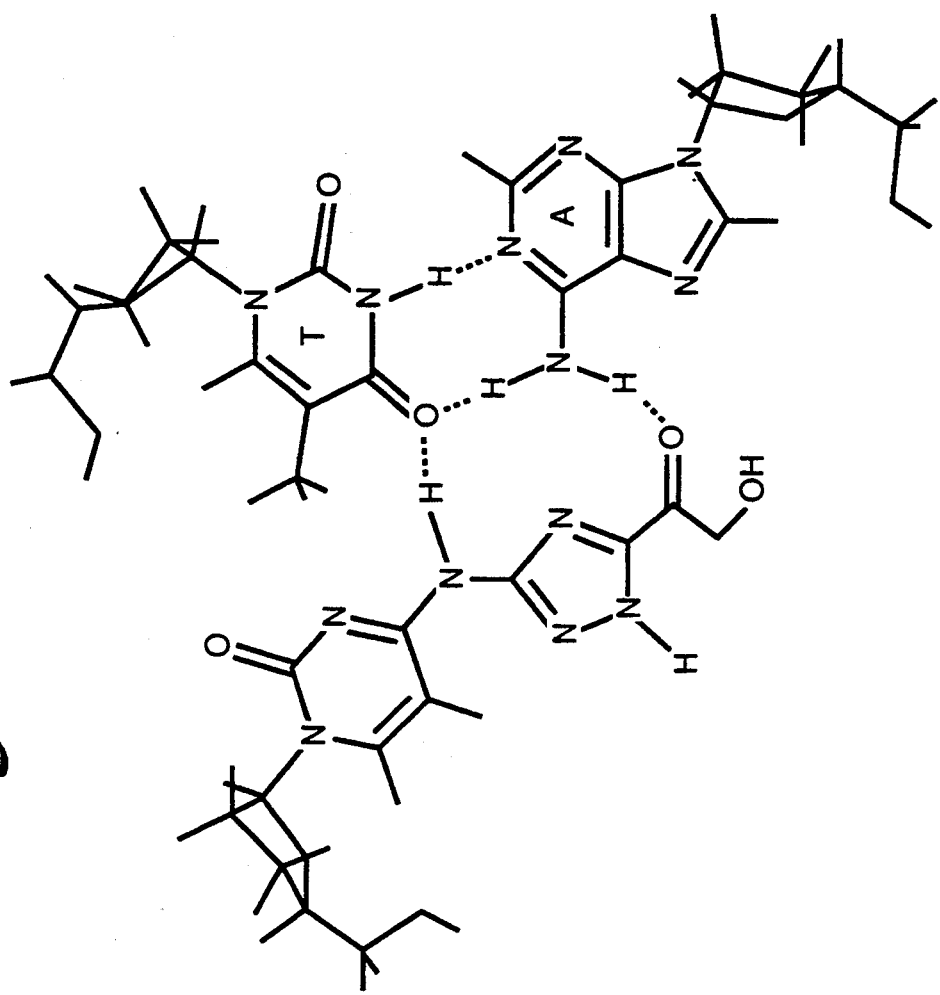
Figure 7B:
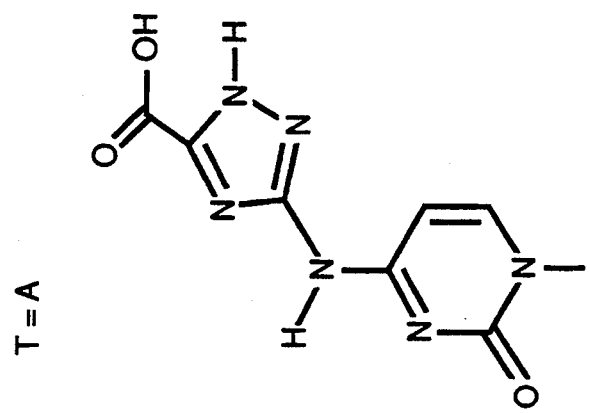

FIG. 7 shows that, in a similar manner, a C residue modified with 3-amino-1,2,4-triazole-5-carboxylic acid can participate in triplex formation with a T-A base pair of double-stranded DNA to provide the triplex structure identified as DNA 163.

It will be appreciated that various modifications may be made in the invention as described above. Thus, as earlier noted, the invention is applicable to oligonucleotide analogs. This includes, as examples, and without intending to be limited thereby, the following:

(a) oligodeoxyribonucleoside and oligo-2'-O-methylribonucleoside methylphosphonates, (b) oligodeoxyribonucleotide and oligo-2'-O-methylribonucleotide phosphorothioates, (c) oligodeoxyribonucleotide and oligo-2'-O-metehylribonucleotide phosphotriesters, (d) oligodeoxyribonucleotide and oligo-2'-O-methylribonucleotide phosphoramidates and (e) 2'-O-methylribooligonucleotides.

In summary, the invention as described above shows that a single deoxycytidine residing in an oligodeoxyribonucleotide or analog thereof which also contains 5-methyldeoxycyctidines can be selectively derivatized with various alkyl amines by sodium bisulfite-catalyzed transamination. Selective transamination results because 5-methylcytosine, unlike cytosine, does not form a bisulfite adduct. When the reaction is carried out at pH 7.1, transamination in the oligomer appears to occur to greater than 95% with little or no deamination. This procedure can be used to introduce aminoalkyl or carboxyalkyl side chains at the $N^4$-position of a single deoxycytidine in oligonucleotides. Thus side chains provide potentially reactive amine or carboxy groups which can serve as sites for further conjugation of the oligomer with a variety of useful functional groups. Oligonucleotides which carry these side chains form duplexes and triplexes with appropriate complementary single-stranded or double-stranded oligodeoxyribonucleotide target molecules. The stabilities of the duplexes are similar to those formed by unmodified oligomers, whereas the stability of the triplexes is approximately 18° C. lower than that formed by unmodified oligomers.

Listed below are the various literature references noted in the background section of this specification:

1. Goodchild, J. (1990) Conjugates of Oligonucleotides and Modified Oligonucleotides: A Review of Their Synthesis and Properties. *Bioconjugate Chemistry*, 1:165–187.

2. Uhlmann, E. and Payman, A. (1990) Antisense Oligonucleotides: A New Therapeutic Principle. *Chemical Reviews*, 90:544–584.

3. Englisch, U. and Gause, D. H. (1991) Chemically Modified Oligonucleotides as Probes and Inhibitors. *Angew. Chem. Int. Ed. Engl.*, 30:613–629.

4. Zuckerman, R. Corey, D. and Schultz, P. (1987) Efficient Methods for Attachment of Thiol Specific Probes to the 3' Ends of Synthetic Oligodeoxyribonucleotides. *Nucleic Acids Res.*, 16:5305–5321.

5. Nelson, P. S., Frye, R. A. and Liu, E. (1989) Bifunctional Oligonucleotide Probes Synthesized Using a Novel CPG Support are able to Detect Single Base Pair Mutations. *Nucleic Acids Res.*, 17:7187–7194.

6. Haralambidis, J., Duncan, L., Angus, K. and Tregear, G. W. (1990) The Synthesis of Polyamide-Oligonucleotide Conjugate Molecules. *Nucleic Acids Res.*, 18, 493–498.

7. Asseline, U. and Thuong, N. T. (1990) New Solid-Phase for Automated Synthesis of Oligonucleotides Containing an Amino-Alkyl Linker at Their 3'-End. *Tetrahedron Lett.*, 31:81–84.

8. Gupta, K. C., Sharma, P., Kumar, P. and Sathyanarayana, S. (1991) A General Method for the Synthesis of 3'-Sulfhydryl and Phosphate Group Containing Oligonucleotides. *Nucleic Acids Res.*, 19:3019–3025.

9. Bonfils, E. and Thuong, N. T. (1991) Solid Phase Synthesis of 5',3'-Bifunctional Oligodeoxyribonucleotides Bearing a Masked Thiol Group at the 3'-End. *Tetrahedron Lett.*, 32:3053–3055.

10. Chu, B. C. F., Wahl, G. M. and Orgel, L. E. (1983) Derivatization of Unprotected Polynucleotides. *Nucleic Acids Res.*, 11:6513–6529.

11. Chollet, A. and Kawashima, E. H. (1985) Biotin Labeled Synthetic Oligodeoxyribonucleotides: Chemical Synthesis and Uses as Hybridization Probes. *Nucleic Acids Res.*, 131529–1541.
12. Teare, J. and Wollenzien, P. (1989) Specificity of the Site Directed Psoralen Addition to RNA. *Nucleic Acids Res.*, 17:3359–3372.
13. Bhan, P. and Miller, P. S. (1990) Photochemical Crosslinking of Psoralen-Derivatized Oligonucleoside Methylphosphonates with Synthetic DNA Containing a Promoter for T7 RNA Polymerase. *Bioconjugate Chemistry*, 1:82–88.
14. Gottikh, M., Asseline, U. and Thuong, N. T. (1990) Synthesis of Oligonucleotides Containing a Carboxyl Group at Either Their 5'-End or 3'-End and Their Subsequent Derivatization by an Intercalcating Agent. *Tetrahedron Lett.*, 31:6657–6660.
15. Agrawal, S. and Tang, J. -Y. (1990) Site-Specific Functionalization of Oligodeoxynucleotides for Non-Radioactive Labelling. *Tetrahedron Lett.*, 31:1543–1546.
16. Agraal, S. and Zamecnik, P. C. (1990) Site-Specific Functionalization of Oligonucleotides for Attaching Two Different Reporter Groups. *Nucleic Acids Res.*, 18:5419–5423.
17. Gryaznov, S. M. and Potapov, V. K. (1991) A New Approach to the Synthesis of Oligodeoxyribonucleotides with Alkylamino Groups Linked to Internucleotide Phosphate Groups, *Tetrahedron Lett.*, 30:3715–3718.
18. Murakami, A., Nakaura, M. Nakatsuji, Y. Nagahara, S., Trang-Cong, Q. and Makino, K. (1991) Fluorescent-labeled Oligonucleotide Probes: Detection of Hybrid Formation in Solution by Fluorescence Polarization Spectroscopy. *Nucleic Acids Res.*, 19:4097–4102.
19. Agrawal, S., Christodoulou, C. and Gait, M. J. (1986) Efficient Methods for Attaching Non-Radioactive Labels to the 5' Ends of Synthetic Oligodeoxyribonucleotides. *Nucleic Acids Res.*, 14:6227–6245.
20. Roduit, J. -P., Shaw, J., Chollet, A. and Chollet A. (1987) Synthesis of Oligodeoxyribonucleotides Containing an Aliphatic Amino Linker Arm at Selected Adenine Bases and Derivatization with Biotin. *Nucleosides & Nucleotides*, 6:349–352.
21. Sproat, B. S., Lamond, A. I., Beijar, B., Neuner, P. and Ryder, U. (1989) Highly Efficient Chemical Synthesis of 2'-O-Methyloligoribonucleotides and Tetrabiotinylated Derivatives: Novel Probes that are Resistant to Degradation by RNA or DNA Specific Nucleases. *Nucleic Acids Res.*, 17:3373–3386.
22. Nelson, P., Sherman-Gold, R. and Leon, R. (1989) A New and Versatile Reagent for Incorporating Multiple Primary Aliphatic Amines into Synthetic Oligonucleotides. *Nucleic Acids Res.*, 17:7179–7186.
23. Pei, D., Ulrich, H. D. and Schultz, P. G. (1991) A Combinatorial Approach Toward DNA Recognition. *Science*, 253:1408–1411.
24. Shapiro, R. and Weigras, J. M. (1970) Bisulfite-Catalyzed Transamination of Cytosine and Cytidine. *Biochem. Biophys. Res. Comm.*, 40:839–843.
25. Maniatis, T., Fritsch, E. F. and Sambrook, J. (1982) *Molecular Cloning, A Laboratory Manual*, Cold Spring Harbor Laboratory, Cold Spring Harbor, N.Y., p. 396.
26. Draper, D. E. (1984) Attachment of Reporter Groups to Specific, Selected Cytidine Residues in RNA Using a Bisulfite-Catalyzed Transamination Reaction. *Nucleic Acids Res.*, 12:989–1002.
27. Hayatsu, H. (1976) Reaction of Cytidine with Semicarbazide in the Presence of Bisulfite. A Rapid Modification Specific for Single-Stranded Polynucleotides. *Biochemistry*, 15:2677–2682.
28. Negishi, K., Harada, F., Nishimura, S. and Hayatsu, H. (1977) A Rapid Cytosine-Specific Modification of *E. coli* tRNA$^{tMet}$ by Semicarbazide-Bisulfite, A Probe for Polynucleotide Conformations. *Nucleic Acids Res.*, 4:2283–2292.
29. Draper, D. E. and Gold, L. M. (1980) A Method for Linking Fluorescent Labels to Polynucleotides: Application to Studies of Ribosome-Ribonucleic Acid Interactions. *Biochemistry*, 19:1774–1781.
30. Schylman, L. H., Pleka, H. and Reines, S. A. (1981) Attachment of Protein Affinity-Labeling Reagents of Variable Length and Amino Acid Specificity to *E. coli* tRNA$^{tMet}$. *Nucleic Acids Res.*, 9:1203–1217.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTTCTTTTT C         1 1

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO:2:

CTTCTTTTTT CTTTT 15

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:3:

CTTCTTTTTT N 11

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

CTTCTTTTTT NTTTT 15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

AAAAGAAAAA AGAAG 15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:6:

GAAGAAAAAA GAAAA 15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (i i) MOLECULE TYPE: DNA (genomic)

(x i) SEQUENCE DESCRIPTION: SEQ ID NO:7:

CTTCTTTTTT NTTTT 15

The scope of the invention is defined in the following claims wherein:

What is claimed is:

1. A method for preparing an oligonucleotide triplex, comprising the steps of:
   a) forming a linker arm-conjugated oligonucleotide by selectively introducing, via bisulfite-catalyzed transamination, a linker arm at a specific deoxycytidine site within an oligonucleotide which also contains one or more 5-methyldeoxycytidine residues and
   b) hybridizing said linker arm-conjugated oligonucleotide to a target oligonucleotide duplex to form said oligonucleotide triplex.

2. The method of claim 1 wherein said linker arm is an aminoalkyl or carboxyalkyl linker arm.

3. The method of claim 1 wherein said oligonucleotide is an oligodeoxyribonucleotide.

4. The method of claim 1 wherein said target oligonucleotide duplex is an oligodeoxyribonucleotide duplex.

5. A method for preparing an oligonucleotide triplex, comprising the steps of:
   a) forming a linker arm-conjugated oligonucleotide by selectively introducing, via bisulfite-catalyzed transamination, a linker arm at a specific deoxycytidine site within an oligonucleotide which also contains one or more 5-methyldeoxycytidine residues, wherein said transamination is performed with a reactant selected from the group comprising 4-aminobutyric acid; 1,4-diaminobutane; 1-aminobutane; or 3-aminobenzoic acid; and
   b) hybridizing said linker arm-conjugated oligonucleotide to a target oligonucleotide duplex to form said oligonucleotide triplex.

* * * * *